United States Patent
Whittaker et al.

(10) Patent No.: US 11,246,870 B2
(45) Date of Patent: Feb. 15, 2022

(54) MPO INHIBITORS FOR USE IN MEDICINE

(71) Applicant: AstraZeneca AB, Södertälje (SE)

(72) Inventors: Andrew Whittaker, Cambridge (GB); Hitesh Jayantilal Sanganee, Cambridge (GB)

(73) Assignee: ASTRAZENCA AB, Södertälje (SE)

( * ) Notice: Subject to any disclaimer, the term of this patent is extended or adjusted under 35 U.S.C. 154(b) by 0 days.

(21) Appl. No.: 16/631,548

(22) PCT Filed: Jul. 12, 2018

(86) PCT No.: PCT/EP2018/068992
§ 371 (c)(1),
(2) Date: Jan. 16, 2020

(87) PCT Pub. No.: WO2019/016074
PCT Pub. Date: Jan. 24, 2019

(65) Prior Publication Data
US 2020/0206226 A1    Jul. 2, 2020

Related U.S. Application Data

(60) Provisional application No. 62/533,448, filed on Jul. 17, 2017.

(51) Int. Cl.
*A61P 15/10* (2006.01)
*A61K 31/519* (2006.01)
*A61K 31/505* (2006.01)

(52) U.S. Cl.
CPC ............ *A61K 31/519* (2013.01); *A61P 15/10* (2018.01)

(58) Field of Classification Search
CPC ...... A61P 15/10; A61K 31/519; A61K 31/505
See application file for complete search history.

(56) References Cited

U.S. PATENT DOCUMENTS

2016/0152623 A1    6/2016 Inghardt et al.

OTHER PUBLICATIONS

Infertility-cure, 2021, https://www.healthymale.org.au/mens-health/male-infertility.*
Infertility-prevention, 2021, https://americanpregnancy.org/getting-pregnant/infertility/male-infertility-70975/.*
Hirsh. A, Male subfertility, BMJ, 2003, p. 669-672, vol. 327.
Lebig, J. et al, Myeloperoxidase binds to non-vital spermatozoa on phosphatidylserine epitopes, Apoptosis, 2007 (12), 1803-12.
Tremellen, K. Oxidative stress and male infertility—a clinical perspective, Human Reproduction Update 2008, vol. 14, p. 243-58.
Agarwal, A. et al. A unique view on male infertility around the globe. Reproductive Biology and Endocrinology. 2015 (13) 37. p. 1-9.
Elmussareh M et al. Antioxidant therapy for male subfertility: myth or evidence-based? Trends in Urology & Men's Health, Jan./Feb. 2015 p. 35-39.
Zambrano F. et al. Leukocytes coincubated with human sperm trigger classic neutrophil extracellular traps formation, reducing sperm motility. Andrology, 2016 . vol. 106 No. 5. p. 1053-60.
Pullar, J.M et al. Elevated seminal plasma myeloperoxidase is associated with a decreased sperm concentration in young men Andrology, 2017, 5, p. 431-38.

* cited by examiner

*Primary Examiner* — Sun Jae Yoo

(57) ABSTRACT

The present disclosure relates to new therapeutic uses of MPO inhibitors and methods of treatment involving the same.

13 Claims, 6 Drawing Sheets

Figure 1. Table showing baseline andrology-related patient information, semen parameters and leukocyte count

| Age | Primary/secondary infertility | Length of infertility (months) | Clinical Andrology Parameters ||||| CASA Values ||||||||| leukocyte Count (M/ml) |
|---|---|---|---|---|---|---|---|---|---|---|---|---|---|---|---|---|
| | | | Volume (ml) | Count (M/ml) | Total Motility (%) | Morphology (% normal) | TZI | Raw |||| Prepared |||| |
| | | | | | | | | Count (M/ml) | Progression (%) | Rapid (%) | Total Motility (%) | Count (M/ml) | Progression (%) | Rapid (%) | Total Motility (%) | |
| 35 | secondary | 20 | 3.3 | 32 | 45 | 1.5 | 1.3 | 32 | 17 | 22 | 31 | 7.2 | 57 | 60 | 71 | 1.26 |
| 29 | primary | 12 | 2.4 | 46 | 67 | 3.3 | 1.2 | 46 | 48 | 59 | 66 | 22.7 | 69 | 78 | 87 | 0.84 |
| 49 | primary | 15 | 2.5 | 36 | 49 | 2.8 | 1.2 | 36 | 19 | 26 | 32 | 5.1 | 52 | 59 | 63 | 0.89 |
| 43 | secondary | | 2.6 | 16 | 58 | 1.8 | 1.4 | 16 | 16 | 23 | 28 | 2.7 | 42 | 44 | 44 | 0.39 |
| 32 | primary | 24 | 2.6 | 92 | 48 | 2.8 | 1.2 | 92 | 41 | 59 | 66 | 17.2 | 55 | 70 | 79 | 0.93 |
| 33 | secondary | | 3.3 | 33 | 44 | 4.8 | 1.3 | 34 | 18 | 26 | 30 | 1.4 | 47 | 53 | 57 | 0.25 |
| 30 | secondary | 24 | 3.9 | 50 | 48 | 3.5 | 1.3 | 50 | 32 | 35 | 40 | 1.3 | 45 | 48 | 54 | 0.39 |
| 42 | secondary | 56 | 1.6 | 138 | 50 | 0.8 | 1.5 | 138 | 19 | 31 | 31 | 2.9 | 61 | 67 | 76 | 2.2 |
| 38 | primary | 14 | 1.9 | 48 | 49 | 1.8 | 1.4 | 48 | 14 | 20 | 32 | 1.3 | 67 | 39 | 77 | 0.69 |
| 35 | | | 3 | 61 | 45 | 3.8 | 1.3 | 62 | 21 | 26 | 35 | 10.1 | 83 | 87 | 92 | 0.48 |
| 40 | secondary | | 2.6 | 79 | 52 | 0 | 1.4 | 79 | 27 | 31 | 36 | 15.6 | 75 | 85 | 89 | 1.04 |
| 23 | | | 2.3 | 34 | 49 | 1 | 1.3 | 63 | 37 | 57 | 74 | 4.2 | 38 | 74 | 88 | 0.47 |
| 27 | | | 3.2 | 204 | 60 | 4.8 | 1.2 | 109 | 24 | 40 | 51 | 73.5 | 74 | 95 | 96 | 1.08 |
| 31 | secondary | 30 | 3.2 | 156 | 58 | 4 | 1.3 | 117 | 48 | 69 | 77 | 20.8 | 48 | 87 | 90 | 3.22 |
| 24 | | | 6.2 | 23 | 38 | 3.2 | 1.3 | 36 | 21 | 30 | 38 | 26 | 68 | 88 | 89 | 0.18 |
| 25 | primary | | 3.8 | 31 | 44 | 1 | 1.5 | 62 | 11 | 26 | 34 | 11.5 | 51 | 76 | 78 | 2.45 |
| 29 | secondary | 24 | 4.8 | 75 | 47 | 2.8 | 1.3 | 69 | 52 | 80 | 87 | 32.8 | 73 | 86 | 94 | 0.26 |
| 33 | | | | | | | | 81 | 53 | 66 | 73 | 20.7 | 69 | 72 | 93 | 1.01 |
| 32 | primary | 13 | 4.7 | 86 | 32 | 2.8 | 1.3 | 55 | 15 | 26 | 53 | 18.2 | 29 | 44 | 57 | 0.55 |
| 50 | | | 1.2 | 75 | 38 | | | 99 | 40 | 55 | 68 | 1.3 | 11 | 25 | 34 | 1.97 |
| 39 | | | 2.6 | 216 | 20 | | | 72 | 40 | 61 | 67 | 21 | 36 | 53 | 57 | 0.72 |
| 35 | secondary | 54 | 2.5 | 21 | 35 | 5.8 | 1.3 | 33 | 23 | 37 | 48 | 2.2 | 58 | 69 | 71 | 0.37 |
| 42 | | | 4.1 | 112 | 48 | 6.3 | 1.2 | 65 | 54 | 69 | 73 | 46.7 | 38 | 70 | 73 | 0.49 |
| 36 | primary | 18 | 5.4 | 20 | 38 | 1.3 | 1.3 | 38 | 15 | 20 | 34 | 9.4 | 27 | 73 | 78 | 0.29 |
| N/A | | | | | | | | 92.5 | 45 | 69 | 79 | 31.9 | 71 | 88 | 94 | |
| N/A | | | | | | | | 14.2 | 23 | 31 | 35 | 3.1 | 24 | 42 | 53 | |
| N/A | | | | | | | | 33.5 | 18 | 32 | 47 | 6.4 | 31 | 46 | 53 | |
| N/A | | | | | | | | 67.2 | 38 | 58 | 65 | 27 | 38 | 80 | 88 | |
| N/A | | | | | | | | 24.2 | 12 | 17 | 25 | 1.9 | 42 | 46 | 46 | |

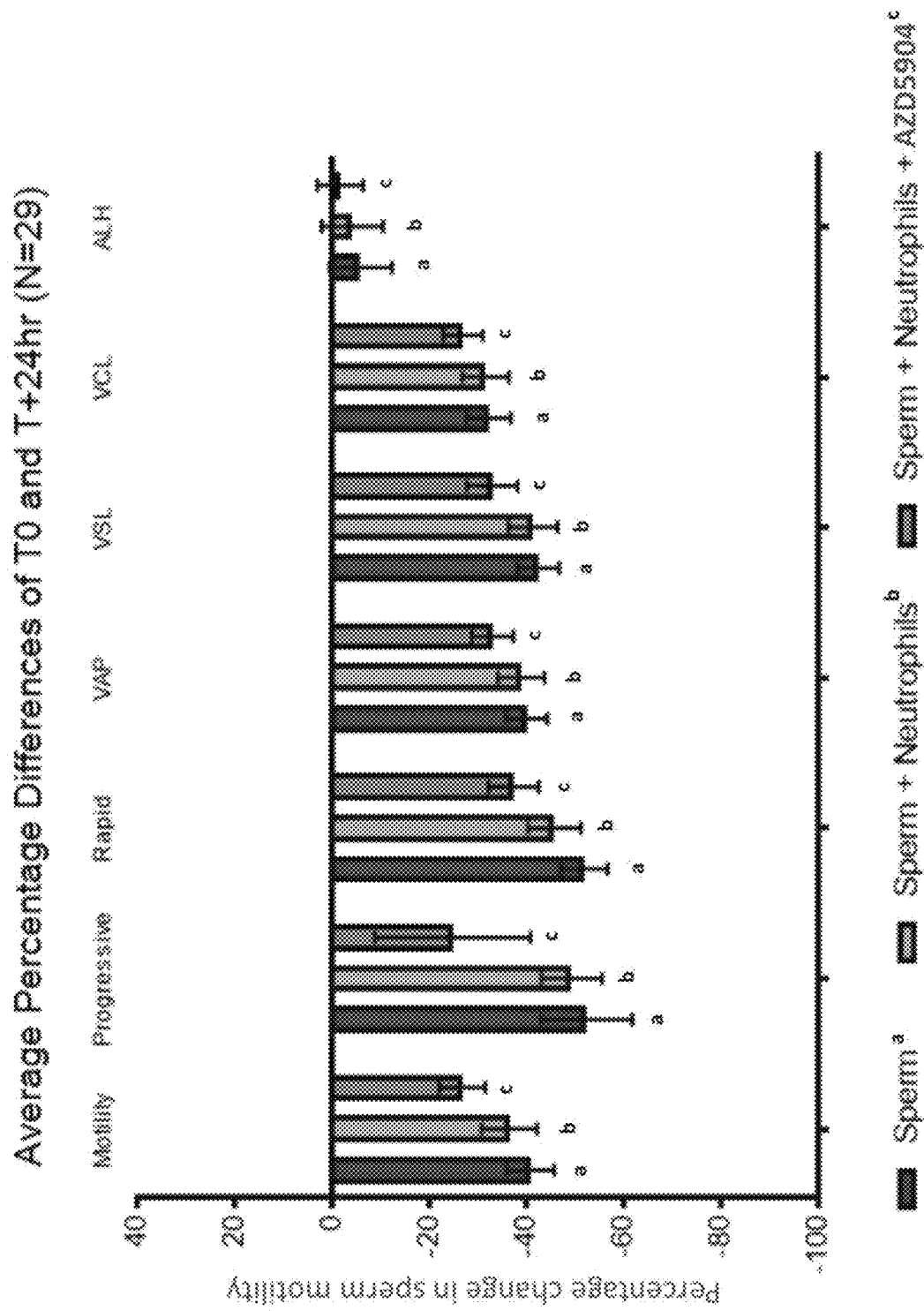
Figure 2. Differences in Sperm Motility Parameters after 24-hour incubation

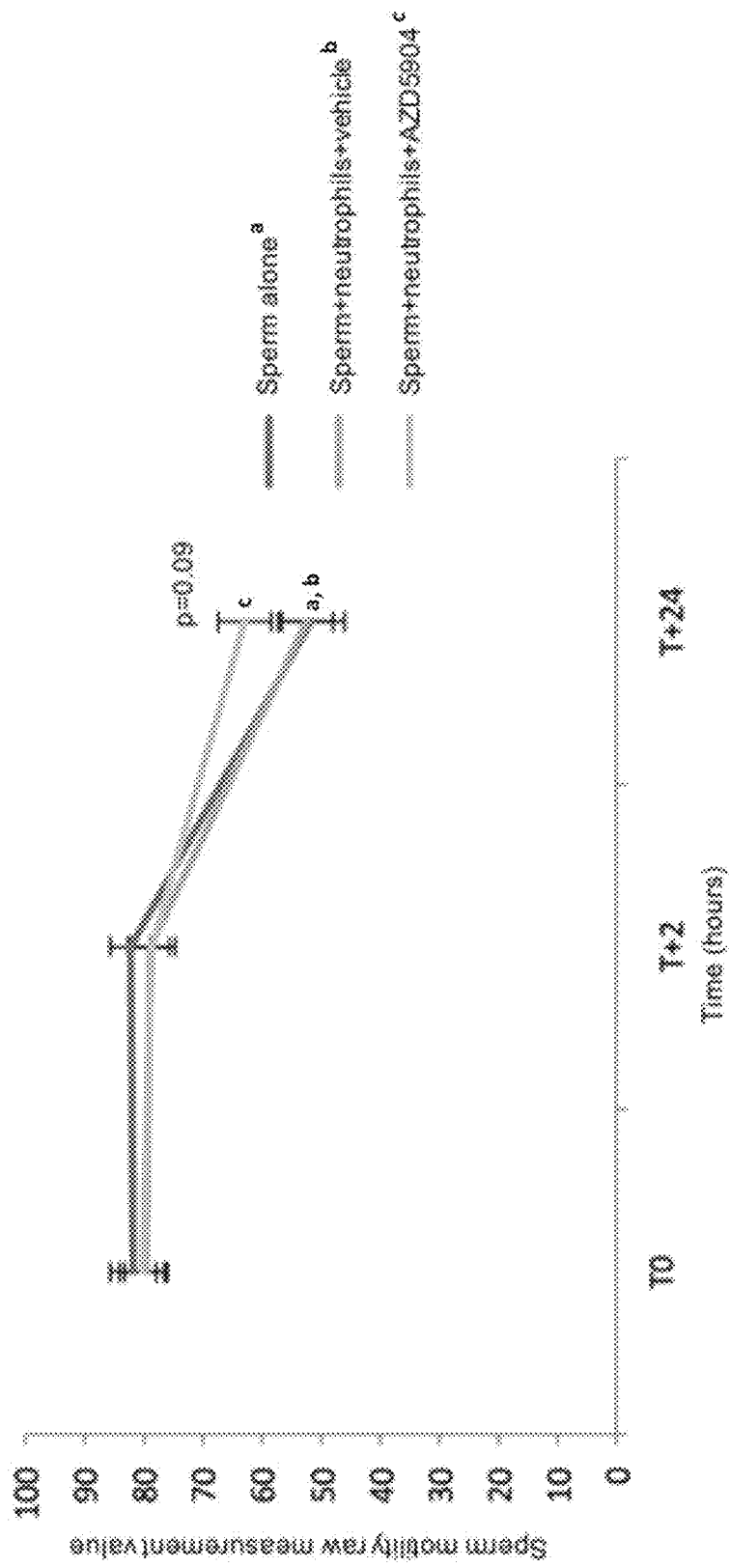
Figure 3. Change in Sperm Motility Parameters after 2h and 24-hour incubation

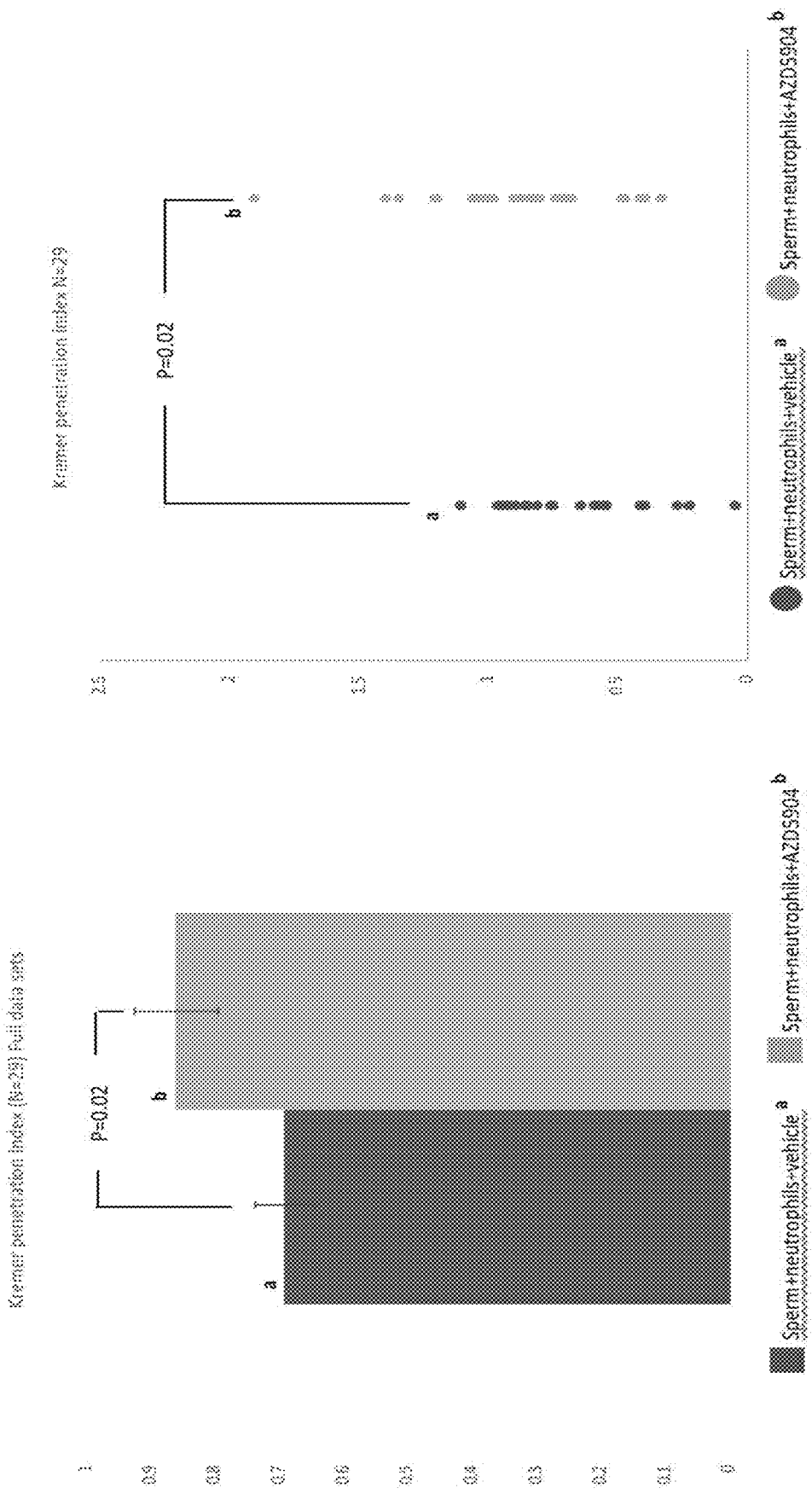
Figure 4. Effect of AZD5904 treatment on Kremer Penetration Assay after 2-hours

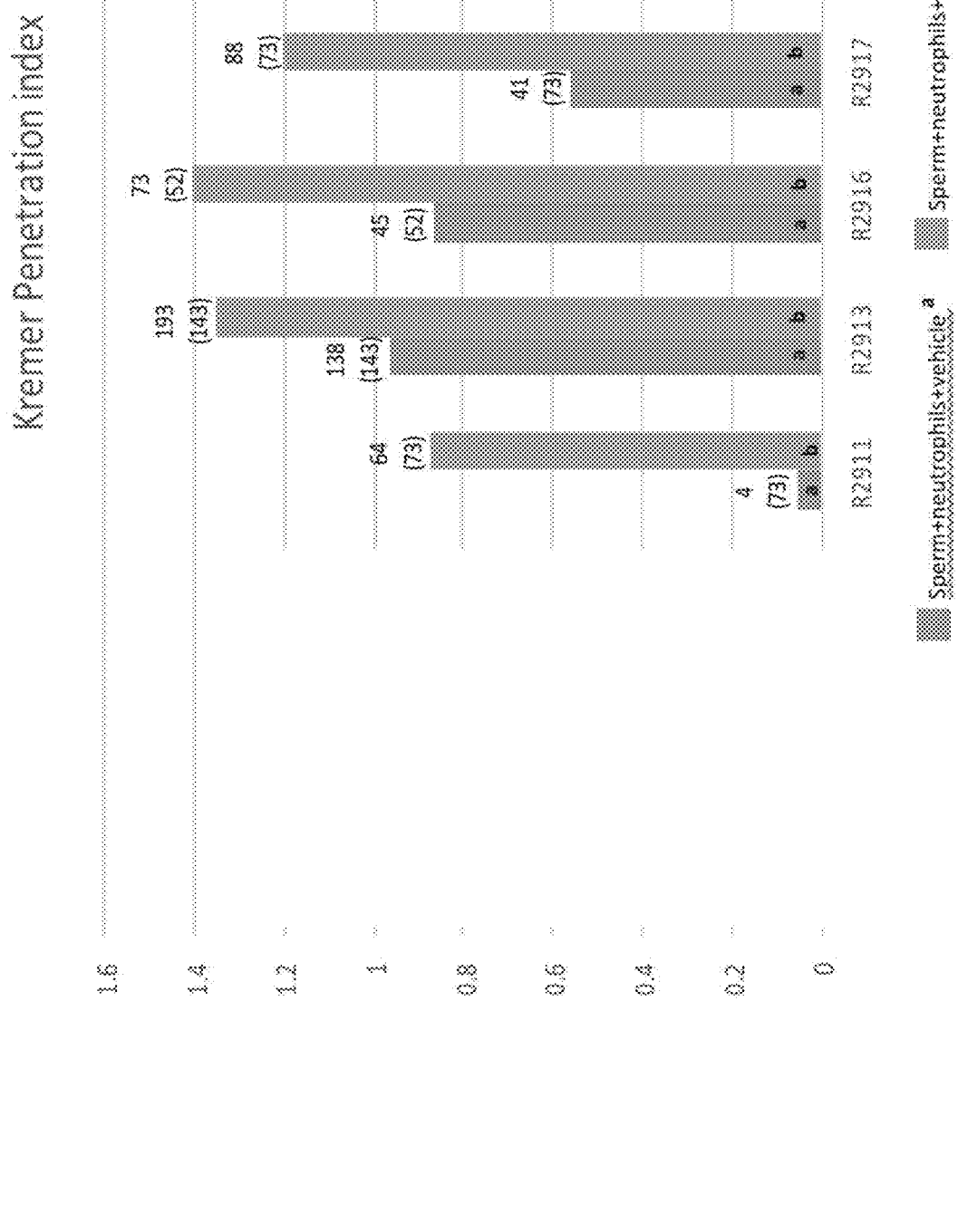
Figures 5. Examples of positive responders to AZD5904 in the Kremer penetration test

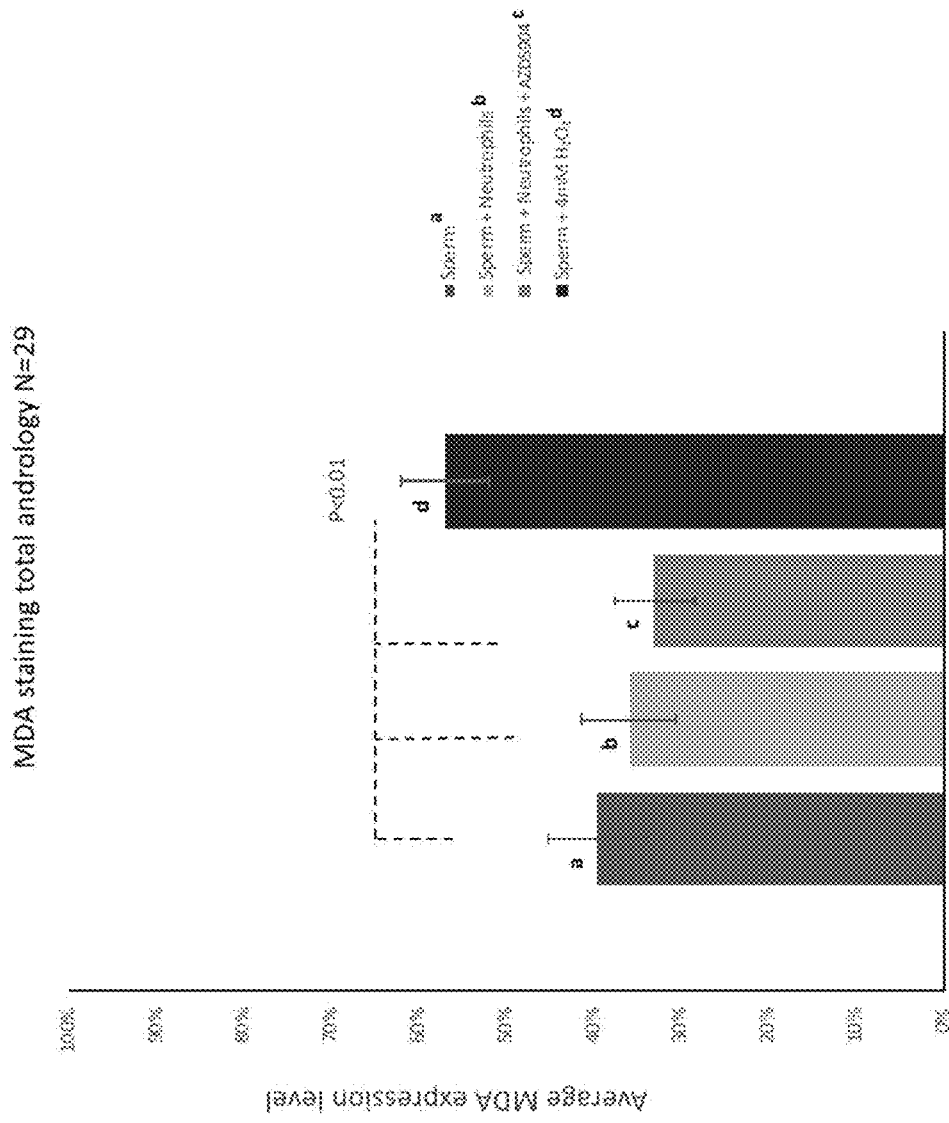
Figure 6 Average MDA staining by flow cytometric analysis

MPO INHIBITORS FOR USE IN MEDICINE

CROSS-REFERENCE TO RELATED APPLICATION

This application is a U.S. National Phase Application of International Application No. PCT/EP2018/068992, filed on Jul. 12, 2018, which claims benefit under 35 U.S.C. § 119(e) of U.S. Provisional Application No. 62/533,448, filed on Jul. 17, 2017. Each of the above-listed applications is incorporated by reference herein in its entirety.

This specification is directed to compounds for use in the treatment of male infertility and methods of treatment of male infertility.

The listing or discussion of an apparently prior published document in this specification should not necessarily be taken as an acknowledgement that the document is part of the state of the art or is common general knowledge.

Infertility affects approximately 15% of couples of reproductive age attempting to conceive worldwide; this roughly equates to around 48.5 million couples. Male infertility is a contributory factor in 50% of infertility problems, and is reported to be the sole cause of infertility in around 20-30% of all cases. These numbers could be an under-representation, as assessment and reporting of male infertility is likely under-reported in many countries.

Male infertility can be caused by various conditions, some of which can be readily identified and corrected, such as ductal obstruction and hypogonadotropic hypogonadism. Other conditions are not reversible, such as bilateral testicular atrophy secondary to viral orchitis. For men who do not have an identifiable cause but do exhibit an abnormal semen profile on analysis, as is the case in many patients, the condition is termed idiopathic male infertility. Standard WHO criteria of semen samples have been defined that are routinely applied during assessment of males undergoing infertility investigations (Table 1). Male factor infertility is commonly defined as an alteration in sperm concentration and/or motility and/or morphology in at least one sample of two sperm analyses, collected 1 and 4 weeks apart. Up to 90% of male infertility cases are due to abnormalities in sperm concentration, morphology or function with no identifiable cause; this is sometimes termed idiopathic oligoasthenoteratozoospermia. In this cohort, oxidative stress is thought to be a significant factor contributing to sperm damage.

Oxidative stress (OS) reflects an imbalance between the generation of reactive oxygen species (ROS) and endogenous antioxidants, and, when an excess of ROS are present, damage to cells and tissues can occur. Epidemiological data from the USA suggests that excessive ROS is a major cause of male factor infertility; 30-40% of infertile men have elevated levels of ROS in their seminal plasma. Spermatozoa are particularly vulnerable to OS as their cell membranes are rich in poly-unsaturated fatty acids (PUFAs) rendering them susceptible to lipid peroxidation. This leads to a rapid loss of intracellular adenosine tri-phosphate (ATP) causing axonemal damage, decreased sperm viability, and increased mid-piece sperm morphological defects, all of which contribute to a reduction in sperm motility. In addition, spermatozoa have inherent deficiencies in intracellular antioxidant enzyme protection and unlike most cell types, spermatozoa have a limited capacity for DNA damage detection and repair.

TABLE 1

WHO criteria for semen analysis
Normal seminal fluid analysis (World Health Organization, 2002)

Volume >2 ml
Sperm concentration >20 million/ml
Sperm motility >50% progressive or >25% rapidly progressive
Morphology (strict criteria) >15% normal forms
White blood cells <1 million/ml
Immunobead or mixed antiglobulin reaction test* <10% coated

*Tests for the presence of antibodies coating the sperm

ROS are produced by both spermatozoa themselves and polymorphonuclear leucocytes (PMNs) such as neutrophils that co-locate with spermatozoa within the testes and epididymis during spermatogenesis and are commonly found in seminal plasma originating from the prostate gland and seminal vesicles. PMNs can produce and release around 1000-fold more ROS than spermatozoa, and thus are likely to be the major source of OS in idiopathic male infertility. Spermatozoa co-incubated with activated neutrophils show a concentration-related reduction in motility with increasing numbers of neutrophils. Neutrophils represent around 60% of the PMN population found in the male genital tract and, when activated, generate superoxide and hydrogen peroxide as part of their oxidative burst. In addition, neutrophils contain large amounts of the haem enzyme myeloperoxidase (MPO) that utilises the hydrogen peroxide generated, to produce hypochlorous acid and other highly reactive oxidants. These oxidants are harmful to human cells and thus have the potential to damage spermatozoa and alter their viability and function. Elevated seminal myeloperoxidase levels have been associated with reduced sperm concentration in young, healthy men. In addition, myeloperoxidase has been shown to play an integral role in neutrophil extracellular trap (NET) formation during NETosis. Human spermatozoa can trigger the release of NETs from neutrophils, which then become firmly attached to the spermatozoa, immobilising them. Treatment of neutrophils with 4-aminobenzoic acid hydrazide, a pre-clinical tool MPO inhibitor, has been shown to significantly reduce spermatozoa-triggered NET formation. To the best of our knowledge, no studies of the use of an MPO inhibitor for the treatment of infertile males has been performed to date.

The current treatment regimen for men experiencing idiopathic infertility starts with lifestyle advice such as cessation of smoking, abstinence from alcohol, optimisation of weight, minimise exposure of testicles to heat and environmental toxins. A selection of over-the-counter oral vitamin and antioxidant based supplements are available. Multiple clinical trials have been performed to assess the effectiveness of these therapies. However, many of these were small, together they exhibit marked methodological and clinical heterogeneity, and overall, they showed mixed results. A recent meta-analysis concluded that the use of oral antioxidants in infertile men could improve sperm quality and pregnancy rates. However, adequately powered robust trials of individual and combinations of antioxidants are needed to guide clinical practice. If despite these measures couples still cannot conceive, assisted reproductive techniques such as intracytoplasmic sperm injection (ICSI) or IVF are used. These techniques are invasive, expensive and not universally available.

There is therefore a clear need for new options for the treatment of male infertility and, in particular, male idiopathic infertility. This is particularly evident in the light of current "off-label" therapy for which efficacy has not been established. It is an objective of the present specification to provide novel therapies for the treatment of male infertility.

In view of the high prevalence of oxidative stress in idiopathic male infertility, the role of myeloperoxidase in neutrophil-mediated generation of potent oxidants, and the emerging data showing the role of MPO in spermatozoa-triggered NETosis we believe that MPO inhibitors may find utility as therapeutic agents for the treatment or prophylaxis of male infertility, and in particular for the treatment of male idiopathic infertility.

Accordingly, in a first aspect the present specification provides a myeloperoxidase (MPO) inhibitor for use in the treatment or prophylaxis of male infertility. The MPO inhibitor for use may be used for the treatment of male idiopathic infertility. The MPO inhibitor for use may be used prophylactically in a subject identified as being disposed to male idiopathic infertility due to identification of elevated levels of reactive oxygen species in a sample of their seminal fluid and/or sperm dysfunction attributable as secondary to oxidative stress.

In a second aspect, the present specification provides a method of treatment or prophylaxis of infertility in a male patient in need thereof, comprising administering to said patient a therapeutically effective amount of a MPO inhibitor. The male patient in need will typically be a patient with male idiopathic infertility or will be a subject identified as being disposed to male idiopathic infertility.

In a third aspect, the present specification provides a myeloperoxidase inhibitor, or a pharmaceutically acceptable salt or solvate thereof, for use in the manufacture of a medicament for the treatment or prophylaxis of male infertility.

In a fourth aspect, the present specification provides a pharmaceutical composition comprising a myeloperoxidase inhibitor or a pharmaceutically acceptable salt or solvate thereof, for use in the treatment or prophylaxis of male infertility, in particular for use in male idiopathic infertility.

In a fifth aspect there is provided a kit comprising a pharmaceutical composition comprising a myeloperoxidase inhibitor or a pharmaceutically acceptable salt or solvate thereof, and instructions for use of the pharmaceutical composition for the treatment or prophylaxis of male idiopathic infertility.

In preferred aspects described herein and above the male patient in need is patient with male idiopathic infertility or, in the case of prophylaxis, a patient identified as being disposed to male idiopathic infertility.

In preferred aspects described herein and above the male patient is human. The present invention also provides use of a myeloperoxidase inhibitor for the treatment of male infertility in non-human land mammals, for example in members of the Canidae, Felidae, Bovidae, Equidae, Suidae, Camelini and Cervidae families.

In embodiments of the aspects presented above, the myeloperoxidase inhibitors for use, for use in methods of treatment, for use in the manufacture of a medicament or provided in a pharmaceutical composition is applied to inhibit spermatozoa triggered NETosis. In such embodiments, the patient may have been screened for treatment by analysis of a sample of their sperm, and found to exhibit evidence of oxidative stress induced damage to sperm for example for a low sperm count/concentration, reduced sperm motility, evidence of sperm DNA fragmentation, presence of sterile leukocytospermia in the context of idiopathic male infertility or a high degree of seminal NETosis.

In embodiments of the aspects presented above, the myeloperoxidase inhibitors for use, for use in methods of treatment, for use in the manufacture of a medicament or provided in a pharmaceutical composition is applied to inhibit oxidative stress via inhibition of the production of reactive oxygen species and/or downstream reactive oxygen species-mediated products. Thus the MPO inhibitor for use, or for use in a method of treatment, may be used to inhibit the production of reactive oxygen species hypohalous acids such as hypochlorous acid as well as other MPO mediated products including but not limited to 3-chlorotyrosine and 3-nitrotyrosine.

Additionally or alternatively, the patient in need of treatment may have been diagnosed as having male idiopathic infertility, for example after failure to conceive in partnership with a fertile partner for a period of 6-months or more. In the case of prophylactic intervention, the patient in need thereof may have been analysed for their propensity to suffer from male idiopathic infertility by analysis of their sperm characteristics or other physiological parameters, for example a patient with a certain profile of markers/characteristics in a sperm sample indicating oxidative stress-induced sperm dysfunction, or abnormally high levels of seminal oxidative stress (such as reduced total antioxidant capactity, elevated reactive oxygen species, or increased lipid peroxidation), or seminal leukocytospermia (by WHO definition) in the context of subnormal male fertility, or a high degree of seminal NETosis.

In embodiments of the aspects presented above, there is provided a method of restoring fertility in a male subject identified as idiopathic infertility patient in need thereof, involving dosing of a therapeutically effective amount of a MPO inhibitor. In one embodiment, the method of treatment of male idiopathic infertility or method of restoring fertility in a male idiopathic infertility patient, involving dosing of a therapeutically effective amount of a MPO inhibitor for inhibiting oxidative stress induced damage to sperm and preventing spermatozoa-triggered NETosis.

The myeloperoxidase inhibitors for use, for use in methods of treatment, for use in the manufacture of a medicament or provided in a pharmaceutical composition may be selected from any known MPO inhibitor. In preferred embodiments of the aspects above the MPO inhibitor is selected from the MPO inhibitors described in WO 2006062465 A1, WO 2008152420 A1, and/or WO 2016087338 A1.

In embodiments, the myeloperoxidase inhibitor is 3-[[(2R)-tetrahydrofuran-2-yl]methyl]-2-thioxo-7H-purin-6-one (AZD5904), or a pharmaceutically acceptable salt or solvate thereof.

In embodiments, the myeloperoxidase inhibitor is 1-(2-isopropoxyethyl)-2-thioxo-2,3-dihydro-1H-pyrrolo[3,2-d]pyrimidin-4(5H)-one, or a pharmaceutically acceptable salt or solvate thereof.

In embodiments, the myeloperoxidase inhibitor is a compound of Formula (I)

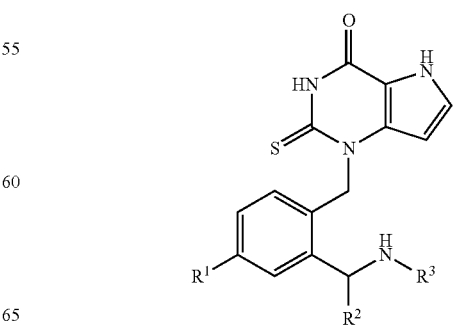

wherein

R¹ is H, F, Cl or CF₃;

R² is H, CH₃ or C₂H₅; and

R³ is H, CH₃, C₂H₅, n-propyl, isopropyl, n-butyl, isobutyl, sec-butyl, tert-butyl, cyclopropyl, cyclopropylmethyl, cyclobutyl, cyclobutylmethyl or cyclopentyl;

or a pharmaceutically acceptable salt or solvate thereof.

In one embodiment, the compound of Formula (I) is selected from:

1-{2-[(1R)-1-aminopropyl]-4-chlorobenzyl}-2-thioxo-1,2,3,5-tetrahydro-4H-pyrrolo[3,2-d]pyrimidin-4-one;

1-[2-(1-aminoethyl)-4-chlorobenzyl]-2-thioxo-1,2,3,5-tetrahydro-4H-pyrrolo[3,2-d]pyrimidin-4-one;

1-{2-[(1R)-1-aminoethyl]-4-chlorobenzyl}-2-thioxo-1,2,3,5-tetrahydro-4H-pyrrolo[3,2-d]pyrimidin-4-one;

1-{2-[(1S)-1-aminoethyl]-4-chlorobenzyl}-2-thioxo-1,2,3,5-tetrahydro-4H-pyrrolo[3,2-d]pyrimidin-4-one;

1-{4-chloro-2-[1-(methylamino)ethyl]benzyl}-2-thioxo-1,2,3,5-tetrahydro-4H-pyrrolo[3,2-d]pyrimidin-4-one;

1-{4-chloro-2-[(ethylamino)methyl]benzyl}-2-thioxo-1,2,3,5-tetrahydro-4H-pyrrolo[3,2-d]pyrimidin-4-one;

1-[2-(aminomethyl)-4-chlorobenzyl]-2-thioxo-1,2,3,5-tetrahydro-4H-pyrrolo[3,2-d]pyrimidin-4-one;

1-{4-chloro-2-[(methylamino)methyl]benzyl}-2-thioxo-1,2,3,5-tetrahydro-4H-pyrrolo[3,2-d]pyrimidin-4-one;

1-(2-{[(cyclobutylmethyl)amino]methyl}benzyl)-2-thioxo-1,2,3,5-tetrahydro-4H-pyrrolo[3,2-d]pyrimidin-4-one;

1-{2-[(cyclobutylamino)methyl]benzyl}-2-thioxo-1,2,3,5-tetrahydro-4H-pyrrolo[3,2-d]pyrimidin-4-one;

1-{2-[(cyclopentylamino)methyl]benzyl}-2-thioxo-1,2,3,5-tetrahydro-4H-pyrrolo[3,2-d]pyrimidin-4-one;

1-(2-{[(2-methylpropyl)amino]methyl}benzyl)-2-thioxo-1,2,3,5-tetrahydro-4H-pyrrolo[3,2-d]pyrimidin-4-one;

1-{2-[(propan-2-ylamino)methyl]benzyl}-2-thioxo-1,2,3,5-tetrahydro-4H-pyrrolo[3,2-d]pyrimidin-4-one;

1-[2-(aminomethyl)-4-(trifluoromethyl)benzyl]-2-thioxo-1,2,3,5-tetrahydro-4H-pyrrolo[3,2 d]pyrimidin-4-one;

1-{2-[(methylamino)methyl]-4-(trifluoromethyl)benzyl}-2-thioxo-1,2,3,5-tetrahydro-4H-pyrrolo[3,2-d]pyrimidin-4-one; and pharmaceutically acceptable salts or solvates thereof.

In the instance where the absolute configuration (R or S) of a single enantiomer of the compound of formula (I) is specified in the list of compounds of Formula (I) above, it is the carbon atom to which R² is attached that is the stereocentre (chiral centre) in question.

4-Aminobenzoic acid hydrazide for use in the treatment of male infertility, in methods of treatment of male infertility, in methods of manufacture of a medicament for the treatment of male infertility or for in pharmaceutical compositions for the treatment of male infertility, as described herein and above, is specifically disclaimed from all aspects and embodiments described herein.

The term "pharmaceutically acceptable" is used to specify that an object (for example a salt, solvate, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002.

Compounds and salts described in this specification may exist in solvated forms and unsolvated forms. For example, a solvated form may be a hydrated form, such as a hemihydrate, a mono-hydrate, a di-hydrate, a tri-hydrate or an alternative quantity thereof. The invention encompasses all such solvated and unsolvated forms of myeloperoxidase inhibitors, for example compounds of Formula (I).

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease. A subject identified as being disposed to male idiopathic infertility and therefore indicated for prophylactic treatment (i.e. a subject in need of prophylaxis) according to the present specification is generally considered to be a patient identified as having elevated levels of reactive oxygen species in a sample of their seminal fluid and/or sperm dysfunction attributable as secondary to oxidative stress. In some embodiments, the identification of a disposition to male idiopathic infertility may be derived from an analysis of a combination of lifestyle factors such as smoking, alcohol consumption, weight and exposure of testicles to heat and environmental toxins.

The term "treatment" is used synonymously with "therapy". Similarly, the term "treat" can be regarded as "applying therapy" where "therapy" is as defined herein.

The term "therapeutically effective amount" refers to an amount of a myeloperoxidase inhibitor as described in any of the embodiments herein which is effective to provide "therapy" in a subject, or to "treat" a disease or disorder in a subject.

The myeloperoxidase inhibitors, and pharmaceutically acceptable salts or solvates thereof, may be administered as pharmaceutical compositions, comprising one or more pharmaceutically acceptable diluents or carriers.

Therefore, in one embodiment there is provided a pharmaceutical composition comprising a myeloperoxidase inhibitor, for example 3-[[(2R)-tetrahydrofuran-2-yl]methyl]-2-thioxo-7H-purin-6-one, 1-(2-isopropoxyethyl)-2-thioxo-2,3-dihydro-1H-pyrrolo[3,2-d]pyrimidin-4(5H)-one or a compound of Formula (I), or a pharmaceutically acceptable salt or solvate thereof, and at least one pharmaceutically acceptable diluent or carrier. The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents. In some preferred embodiments, the MPO inhibitor is to be administered orally. In some preferred embodiments, the MPO inhibitor is to be administered as an extended release form, for example an oral extended release form or a subcutaneous extended release form.

In one embodiment there is provided a pharmaceutical composition comprising a myeloperoxidase inhibitor, for example a compound of Formula (I), 3-[[(2R)-tetrahydrofuran-2-yl]methyl]-2-thioxo-7H-purin-6-one (AZD5904) or 1-(2-isopropoxyethyl)-2-thioxo-2,3-dihydro-1H-pyrrolo[3,2-d]pyrimidin-4(5H)-one, or a pharmaceutically acceptable salt or solvate thereof, and at least one pharmaceutically acceptable diluent or carrier, for use in the treatment of male infertility.

The myeloperoxidase inhibitor will normally be administered to a warm-blooded animal at a unit dose within the range 2.5-5000 mg/m$^2$ body area of the animal, or approximately 0.05-100 mg/kg, and this normally provides a therapeutically-effective dose. A unit dose form such as a tablet or capsule will usually contain, for example 0.1-500 mg of active ingredient. The daily dose will necessarily be varied depending upon the host treated, the particular route of administration, any therapies being co-administered, and the severity of the illness being treated. Accordingly, the practitioner who is treating any particular patient may determine the optimum dosage.

In order to test the hypothesis that MPO inhibitors might be suitable for the treatment of male idiopathic infertility a set of ex-vivo studies were carried out on diagnostic andrology samples collected with consent from patients attending the assisted conception unit (ACU) at Ninewells Hospital in Dundee as detailed below. Experiments were performed to assess various parameters of sperm motility and function as described below.

So that the invention may be better understood, reference to the following Figures is made:

FIG. 1 is a Table illustrating a brief summary of baseline information related to andrology available from the clinic about each patient tested (Age, primary/secondary infertility and length of infertility). Count figures are million per ml (M/ml), WHO reference values are Concentration 15 M/ml, progressive 32%, morphology 4%, leukocytes 1 M/ml).

FIG. 2 is a bar chart shows the percentage differences between CASA measurements at time zero and after 24-hour incubation for motility, progressive motility, rapid motility, average path velocity (VAP), straight line velocity (VSL), curvilinear velocity (VCL) and lateral head displacement (ALH) for the full dataset (n=29). Three conditions were measured; sperm only as the control (left hand column, a), sperm with activated neutrophils (ratio 3:1) with vehicle control (middle column, b) and sperm with activated neutrophils (ratio 3:1) plus 3 μM AZD5904 (right hand column, c). Kruskal-Wallis test shows a positive trend for AZD5904, which does not reach statistical significance for each parameter measured (P>0.1). The error bars represent the standard error of the mean.

FIG. 3 is a line diagram shows the absolute change in overall sperm motility from baseline to 2 h and 24-hour after incubation for the first 11 subjects (highlighted in blue in FIG. 1) who had more pronounced abnormalities in baseline sperm parameters than the next 18 subjects studied. Three conditions were measured; sperm only as the control (a), sperm with activated neutrophils (3:1 ratio) with vehicle control (b) and sperm with activated neutrophils (3:1 ratio) plus 3 μM AZD5904 (c). A two-tailed student t-test between AZD5904 versus vehicle treated groups showed a statistical trend: P=0.09.

FIG. 4 shows the cumulative results from the Kremer penetration assay for the full dataset (n=29) with the results expressed as a ratio to control (sperm only). The error bars represent the standard error of the mean. Student T-test analysis shows that significantly more sperm were found at 1 cm in the AZD5904 treatment group than with the group without drug. P=0.02

FIG. 5 shows examples of data from the Kremer Penetration test at the 2-hour timepoint for four "responder" subjects. Data is expressed as a ratio to control (sperm only). The values above the bars refer to the actual sperm counts at 1 cm; the top number refers to the test condition (Vehicle or AZD5904) while the number in brackets is the control count. The R numbers along the X axis refer to the anonymous patient numbers. A change of at least 0.25 is taken as a meaningful difference in individuals.

FIG. 6 shows the average MDA staining from 29 patients and by in vitro treatment condition: sperm only (a), sperm+neutrophils+vehicle control (b), sperm+neutrophil+AZD5904 (drug) (c) and sperm+4 mM $H_2O_2$ (d). The results for sperm with 4 mM $H_2O_2$ had significantly more staining than the other conditions (P<0.01). The error bars represent the standard error of the mean.

MATERIALS AND METHODS

Experimental Design

A series of 5 tests were carried out on each semen sample acquired (FIG. 1). This approach was used to assess various parameters of sperm motility and function. The methods were validated prior to data collection to ensure reliability and repeatability of results.

Study Subjects/Sample Collection

Surplus diagnostic andrology samples (N=29) were collected with consent from men attending the assisted conception unit (ACU) at Ninewells Hospital in Dundee.

Materials

Non-capacitating media (pH 7.4): 1.8 mM $CaCl_2$, 5.4 mM KCl, 0.8 mM $MgSO_4.7H_2O$, 116.4 NaCl, 1 mM $NaH_2PO_4.2H_2O$, 5.55 mM D-glucose, 2.73 mM sodium pyruvate, 41.75 mM sodium lactate, 25 mM HEPES, 0.3% BSA.

Capacitating Media (pH 7.4): 1.8 mM $CaCl_2$, 5.4 mM KCl, 0.8 mM $MgSO_4.7H_2O$, 116.4 mM NaCl, 1 mM $NaH_2PO_4.2H_2O$, 5.55 mM D-glucose, 2.73 mM sodium pyruvate, 25 mM sodium lactate, 26 mM sodium bicarbonate, 0.3% BSA.

sEBSS (pH 7.4): 1.01 mM $NaH_2PO_4$, 5.4 mM KCl, 0.8 mM $MgSO_4.7H_2O$, 5.5 mM $C_6H_{12}O_6$, 2.5 mM sodium pyruvate, 19 mM sodium lactate, 25 mM sodium bicarbonate, 15 mM HEPES, 1.8 mM $CaCl_2.2H_2O$, 118.4 mM NaCl, 0.3% BSA.

Semen Sample Preparation

Semen samples were collected by masturbation into sterile plastic containers after a minimum of 2 days and a maximum of 7 days sexual abstinence. Semen samples were produced onsite in the ACU and allowed to liquefy for 30 min (37° C.). Prior to sample preparation, 20 μL of raw semen was collected from each sample and 10 μL of this used to prepare semen smears onto clean glass slides (examination of leukocytes). Two slides were made per sample, wrapped in tin foil and stored in a −20° C. freezer until required. Semen samples were then prepared by Percoll Density Gradient Centrifugation (DGC) as described previously (Tardif S, Madamidola OA, Brown SG, Frame L, Lefievre L, Wyatt PG, et al. Human Reproduction 2014; 29:10 2123-2135). Then a maximum of 2 mL per gradient of raw semen was carefully layered on top. The gradient was then centrifuged at 300 g for 20 min. The top most layer which contained only semen was collected into a 1.5 mL Eppendorf tube. This layer was then centrifuged at $17 \times 10^6 \times g$ for 20 min to pellet any cells and debris in the semen layer so that only the seminal fluid would be collected. The supernatant was then collected and centrifuged again at $17,000 \times g$ for 20 min. The supernatant was collected and stored in a $-20°$ C. freezer until required. The pellet from the 80% DGC fraction was collected and washed in 4 mL non-capacitating media for 10 min at 300 g. The supernatant was then discarded. The pellet was collected, resuspended in 1 mL sEBSS solution and incubated ($37°$ C.) for sperm function analysis.

Neutrophil Isolation

Blood samples were collected from volunteer donors into a vacutainer containing EDTA to stop clotting (Zambrano F, Carrau T, Garner U, Seipp A, Taubert A, Felmer R, et al. Fertility and Sterility 2016; 106(5):1053-1060). The blood was mixed with Histopaque 1119 (Sigma, UK) at a ratio of 1:1.2 into a 15 mL falcon tube (Zambrano et al, 2016.). This was then centrifuged at 800 g for 20 min. Following this, the supernatant was discarded and the pellet was transferred into a fresh falcon tube. This tube was then filled to 15 mL with phosphate-buffered saline (PBS) and centrifuged at 300 g for 10 mins. Percoll gradients were prepared firstly by adding 2 mL of 10X PBS to 18 mL Percoll to create a 100% stock. This was then diluted with 1XPBS to create five 4 mL Percoll gradients stocks at concentrations of 65%, 70%, 75%, 80% and 85%. Next, 2 mL of each gradient concentration was layered on top of the other in a 15 mL falcon with 85% at the bottom of the tube and 65% at the top. Following the 10 min centrifugation, the supernatant was discarded again and the pellet was resuspended to 4 mL with PBS. Next, 2 mL of blood was carefully layered on top of the density gradients and centrifuged at 800 g for 20 min. The top most layer was discarded and the 70-80% layers were collected and transferred into a fresh falcon tube. The tube was then filled to 15 mL with PBS and centrifuged for 10 min at 300 g. The supernatant was discarded and the pellet was collected at washed in 2 mL red cell lysis buffer. This step was repeated until the pellet was no longer coloured red with the supernatant discarded each time. Finally, the pellet was resuspended in 1 mL of sEBSS and placed in a $37°$ C. incubator.

Treatment of Sperm with AZD5904 or Vehicle

A 10 mM stock solution of the drug was made up in 100% DMSO. This was then serially diluted to a working concentration of 3 µM using sEBSS as the diluent and stored at $4°$ C. The drug or vehicle was then added to the neutrophils and placed in a $37°$ C. water bath for 10 min. The neutrophils were then added to the sperm in sperm-safe 5 mL Polystyrene round bottom tubes (Falcon) at a ratio of about 1:3. Zymosan at a final concentration of 1 µg/ml was added to activate the neutrophils and incubated for 2 hours at $37°$ C. Four conditions were prepared for the motility assessments, flow cytometry and the Kremer assays: sperm only, sperm+neutrophils+vehicle, sperm+neutrophils+AZD5904 (drug) and sperm+4 mM (final concentration) hydrogen peroxide ($H_2O_2$; positive control for damage).

Motility Assessment

Sperm motility was assessed using the Hamilton-Thorn CASA system. For each condition, a total of 200 cells were counted in at least four different fields of view. Where a sample had very low motility at least 100 cells were counted. The motility parameters were assessed at the start of the co-incubation with neutrophils (time 0), after 2 h and after 24 h. Motility was expressed as a percentage different between time 0 and after 2 h and percentage difference after time 0 and after 24 h for each time point for each sample.

Kremer Penetration Assay

The Kremer penetration test assesses a sperm cell's ability to penetrate and swim through viscous media. This test is also known as the sperm-cervical mucus penetration test. A cervical mucus substitute was made up using 1% methyl cellulose dissolved in capacitating media. The solution was gassed in a $37°$ C. 5% $CO_2$ incubator for 20 min. Then flat capillary tubes (Rectangle Boro Tubing, CM Scientific) were placed in the methyl cellulose solution for a further 20 min to allow the media to flow up the capillary tubes. After the 2 h incubation, 100 µL from each condition was aliquoted into a fresh sperm safe tube. One end of each tube was then blocked using plasticine and then one tube was placed open end first into each test condition. Each sperm safe tube containing a capillary tube was incubated 1 hour at $37°$ C. with 5% $CO_2$. After 1 h, the capillary tubes were removed and the number of cells at 1 cm mark were counted manually. The results were expressed as a ratio to control (sperm only).

Flow Cytometry

Following the 2 h incubation with activated neutrophils, aliquots of 50 µL were taken from all 4 conditions and transferred into 1.5 mL Eppendorf tubes. $H_2O_2$ was used as a positive control. An extra aliquot for a secondary only control was taken from the sperm only tube. The cells (except the secondary only tube) were incubated for 0.5 h at $37°$ C. with an anti-malondialdehyde (MDA) antibody (ab27642, abcam, Cambridge) at a working ratio of 1:50 (Moazamian R, Polhemus A, Connaughton H, Fraser B, Whiting S, Gharagozloo P, Aitken R J. *Mol Hum Reprod* 2015; 21(6):502-15). The tubes were then centrifuged at 300 g for 5 min to pellet the cells and the supernatant was discarded. The cells were then washed twice with sEBSS and the supernatant was discarded each time. A fluorescently tagged goat anti-rabbit secondary (Thermofisher, UK) was then added to all the conditions at a ratio of 1:50 and the tubes were incubated for 10 min at $37°$ C. The cells were pelleted and washed twice as described above. Following the final wash, the pellets were resuspended in 250 µL sEBSS solution and transferred into fresh sperm safe tubes. The level of MDA staining in each condition was then assessed in 10,000 cells using a pre-validated flow cytometry program in a BD LSRFortessa cell analyser. Due to a technical error one sample was unable to be assessed using flow cytometry.

Leukocyte Count

The semen smear slides were removed from the freezer and place in coplin jars filled with Giemsa May-Grünwald solution (diluted 1:20 in distilled water) for 5 min. The slides were then washed in PBS for 1.5 min. Next, the slides were placed into fresh Giemsa May-Grünwald for 20 min then washed with distilled water. They were allowed to air dry before counting. An average count from the two slides per sample was taken. The number of leukocytes counted in the same field as 400 spermatozoa was recorded and the sample leukocyte concentration was calculated using the sperm concentration as per WHO 2010 recommended methods (Cooper TG, Noonan E, von Eckardstein S, Augur J, Baker HWG, Behre HM, et al. Human Reproduction Update, 2010; 16(3):231-245).

RESULTS

Patient Demographics

The Table of FIG. 1 represents the brief summary of baseline information related to andrology available from the clinic about each patient tested (Age, primary/secondary infertility and length of infertility). Raw and prepared sperm parameters were also recorded as well as leukocyte counts.

In more detail, the table shows the ages, length of time the couple have been trying to conceive (length of infertility) and the patient's infertility status (primary or secondary). Semen parameters were measured before (raw) and after (Prep) density gradient centrifugation using the Hamilton-Thorne CASA system, except for raw count which was assess by an Andrologist manually following the WHO manual (World Health Organization. (2010). WHO laboratory manual for the examination and processing of human semen, 5th ed. Geneva: World Health Organization). The red text refers to any sample which presented with parameters lower than normal according to the WHO 2010. The leukocyte count refers to the concentration of leukocytes found in the unprepared semen sample. The R numbers refer to the anonymous patient numbers.

Motility Assessment

Semen samples were collected from patients on the day of their andrology investigations and the motility parameters were recorded. Each sample had three test conditions measured over 24 hours; sperm only, sperm with neutrophils at a ratio of 3:1 plus vehicle control and sperm with neutrophils at a ratio of 3:1 plus 3 μM AZD5904. Motility was measured at time zero, after 2 hours incubation and after 24 hours. FIG. 2 represents the percentage differences between the semen parameters at time zero and after 24-hours of incubation. A Kruskal-Wallis test showed that there was a non-significant trend towards a beneficial relative effect size of approximately 30% for AZD5904 treatment in reducing the impairment on overall sperm motility (p>0.01 for each parameter measured). In order to visualise the differences in motility over time, the data for total motility, rapid and progressive motility were also plotted as line graphs for the first 11 subjects studied, who had more pronounced abnormalities in baseline sperm parameters. FIG. 3 shows the differences over time for motility of the patients tested (N=11).

Kremer Penetration Assay

Each study subject's sperm sample was also assessed for ability to penetrate viscous media using the Kremer penetration test (N=29). FIG. 4 shows the cohort average results for the sperm with activated neutrophils plus vehicle and sperm with activated neutrophils plus AZD5904. The results showed an improvement in sperm penetration through a viscous media for those samples treated with AZD5904 vs vehicle control. Student T-test analysis shows that significantly more sperm were found at 1 cm in the drug treatment group than with the group without drug (p=0.02). There was variation in individual response to treatment with AZD5904 with 15 of the 29 subjects demonstrating what is felt to be a clinically-relevant improvement in sperm penetration following AZD5904. Four examples of positive responders to AZD5904 treatment are shown in FIG. 5.

Flow Cytometry

Following a 2-hour incubation, the levels of MDA was measured using flow cytometry (N=29). Four conditions were measured after a 2-hour incubation; sperm only (control), sperm with neutrophils at a ratio of 3:1 plus vehicle control, sperm with neutrophils at a ratio of 3:1 plus 3 μM AZD5904 (Drug) and sperm with 4 mM $H_2O_2$. FIG. 6 shows the average MDA staining for all 4 conditions. A one-way ANONA showed that the sperm with 4 mM $H_2O_2$ stained significantly more than the other conditions tested (P<0.01).

Analysis of Results

AZD5904 was chosen as a representative MPO inhibitor due to its extensive prior clinical profiling in man and the good safety profile observed therein. It is expected that the results obtained with this representative MPO inhibitor will also be obtained with other potent, selective, MPO inhibitors such as, but not limited to, the compounds described in WO 2006062465 A1 (that discloses 1-(2-isopropoxyethyl)-2-thioxo-2,3-dihydro-1H-pyrrolo[3,2-d]pyrimidin-4(5H)-one (also known as AZD3241), WO 2008152420 A1, and/or WO 2016087338 A1 (that describes the compounds of Formula (I) specifically disclosed herein).

In more detail, AZD5904 is a potent ($IC_{50}$ of 140 nM) irreversible inhibitor of human MPO with similar potency in mouse and rat. It is 10 to 19-fold selective compared to the closely related lactoperoxidase and thyroid peroxidase; >70-fold to a broad panel of other enzymes, ion channels, and receptors. In isolated human neutrophils, 1 μM inhibited PMA stimulated HOCl by >90%. In rats, a plasma concentration of ~5 μM decreased the in vivo formation of glutathione sulphonamide (a product of the reaction of HOCl with glutathione) from in situ zymosan activated peritoneum neutrophils. AZD5904 has been administered orally to healthy volunteers in single doses of up to 1200 mg (1400 mg with extended release, ER, formulation) and multiple doses of up to 325 mg TID (600 mg BID for 10 days with ER formulation). In total, 181 subjects have been dosed in five Phase 1 studies. No overtly drug-related adverse event has yet been identified.

The results obtained in the tests described in the present application relating to the activity of an MPO inhibitor on sperm properties that are presented in the accompanying figures illustrate the effects of a representative MPO inhibitor (AZD5904) on sperm obtained from subjects suffering from male idiopathic infertility. In total, the sperm samples from 29 subjects were tested. While the individual results showed a degree of variability, cumulatively, and despite the small (pilot study) sample size, the data shows a positive trend for improvement in overall sperm motility at 24 hours following administration of AZD5904 to a co-incubation of human sperm with activated human neutrophils vs vehicle.

The Kremer Penetration test is a particularly useful test for assessing the influence of a drug on sperm motility. This is because it evaluates the sperms ability to penetrate and swim through media with similar viscosity to that found in the female tract, which the sperm would naturally swim through in vivo (Ivic A, Onyeaka H, Girling A, Brewis IA, Ola B, Hammadieh H et al. *Human Reproduction* 2002; 17(1):143-149). The sperm penetration test provides objective, quantitative, and reproducible information about the functional status of sperm and has been shown to be a valuable marker of fertility, especially in male factor infertility (see Eggert-Krause W, Gerhard I, Tilgen W, Runnebaum B. Fertil Steril 1989; 52: 1032-1040; Eggert-Krause W, Leinhos G, Gerhard I, Tilgen W, Runnebaum B. Fertil Steril 1989; 51: 317-323; Polansky F F and Lamb E J. Fertil Steril 1989; 51(2): 215-28; Ola B, Afnan M, Papaioannou S, Sharif K, Bjorndahl L, Coomarasamy A. Hum Reprod 2003; 18(5): 1037-46). The cervical mucus substitute used in the study, created using methylcellulose and capacitating media, has been shown to be a suitable surrogate for human cervical mucus (Ivic et al, 2002; Tang S, Garrett C, Baker H W. Human Reprod 1999; 14(11): 2812-7). The results from this preliminary study showed that after 2-hours treatment of sperm co-incubated with activated neutrophils, a statistically significant improvement in sperm penetration was obtained with AZD5904 treatment versus vehicle (p=0.02). On an individual subject level, AZD5904 provided a clinically-relevant beneficial effect in just over 50% of patients tested (15 responders from the 29 patients evaluated), while a further 8 subjects showed a smaller improvement. Attempts were made to identify phenotypic or demographic factors that were associated with a positive response to AZD5904 treatment, but the sample size was too small to allow this. Further work involving a larger number of subjects is ongoing.

While a precise mechanism of effect through which MPO inhibition delivers an improvement in sperm properties remains to be established, the differences in the motility tests were more evident following the 24 hour incubation.

To summarise, the results from a preliminary investigation of the potential of MPO inhibitors for the treatment of male idiopathic infertility disclosed above show that in vitro treatment of human sperm with an MPO inhibitor is associated with a strong trend towards a beneficial effect on protecting sperm from neutrophil mediated damage with regards to improvements in overall sperm motility after 24-hours and sperm penetration after just 2-hours. In 15 of 29 subjects the improvement in the Kremer Penetration test was adjudged to be clinically important, and overall MPO inhibitor treatment led to a statistically significant improvement in sperm penetration in the Kremer Test. These results provide strong support for the proposition that MPO inhibitors, such as AZD5904, may be useful for the treatment of male idiopathic infertility. Expanded studies to confirm the results obtained in these initial studies are ongoing.

The invention claimed is:

1. A method of treatment of male infertility in a patient in need thereof, comprising administering to said patient a therapeutically effective amount of a myeloperoxidase (MPO) inhibitor.

2. The method of treatment according to claim 1, wherein the patient is suffering from male idiopathic infertility.

3. The method of treatment according to claim 1, wherein the patient is a human patient.

4. The method of treatment according to claim 1, wherein the patient is a non-human land mammal.

5. The method of treatment according to claim 1, wherein the MPO inhibitor inhibits oxidative stress-induced sperm damage and/or prevents spermatozoa triggered NETosis.

6. The method of treatment according to claim 1, wherein the myeloperoxidase inhibitor is 1-(2-isopropoxyethyl)-2-thioxo-2,3-dihydro-1H-pyrrolo[3,2-d]pyrimidin-4(5H)-one:

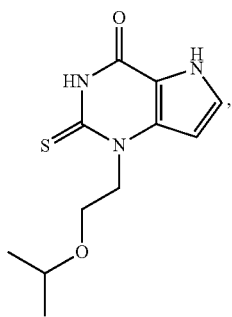 [SMILES: CC(C)OCCn1c(=S)[nH]c(=O)c2[nH]ccc21]

or a pharmaceutically acceptable salt or solvate thereof.

7. The method of treatment according to claim 1, wherein the myeloperoxidase inhibitor is 3-[[(2R)-tetrahydrofuran-2-yl]methyl]-2-thioxo-7H-purin-6-one:

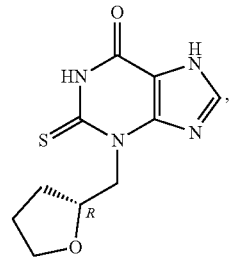

or a pharmaceutically acceptable salt or solvate thereof.

8. The method of treatment according to claim 1, wherein the myeloperoxidase inhibitor is a compound of formula (I):

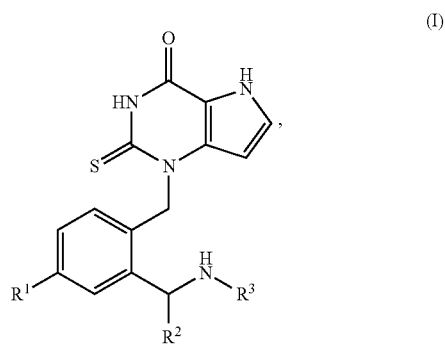

wherein:

$R^1$ is H, F, Cl or $CF_3$;

$R^2$ is H, $CH_3$ or $C_2H_5$; and $R^3$ is H, $CH_3$, $C_2H_5$, n-propyl, isopropyl, n-butyl, isobutyl, sec-butyl, tert-butyl, cyclopropyl, cyclopropylmethyl, cyclobutyl, cyclobutylmethyl or cyclopentyl;

or a pharmaceutically acceptable salt or solvate thereof.

9. The method of treatment according to claim 1, wherein the myeloperoxidase inhibitor is:

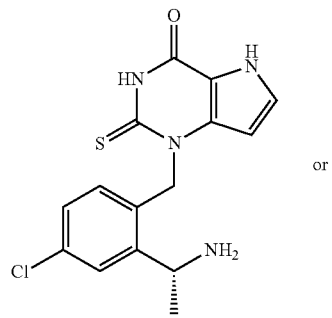

or

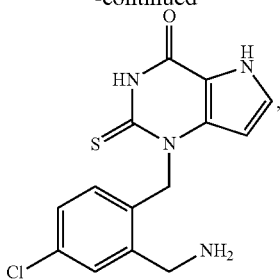

or a pharmaceutically acceptable salt or solvate thereof.

10. The method of treatment according to claim 6, wherein the myeloperoxidase inhibitor is 1-(2-isopropoxyethyl)-2-thioxo-2,3-dihydro-1H-pyrrolo[3,2-d]pyrimidin-4(5H)-one:

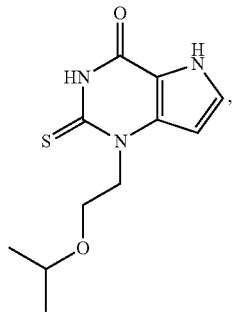 [SMILES: CC(C)OCCn1c(=S)[nH]c(=O)c2[nH]ccc21]

or a pharmaceutically acceptable salt thereof.

11. The method of treatment according to claim 7, wherein the myeloperoxidase inhibitor is 3-[[(2R)-tetrahydrofuran-2-yl]methyl]-2-thioxo-7H-purin-6-one:

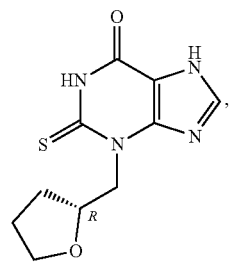

or a pharmaceutically acceptable salt thereof.

12. The method of treatment according to claim 8, wherein the myeloperoxidase inhibitor is the compound of formula (I):

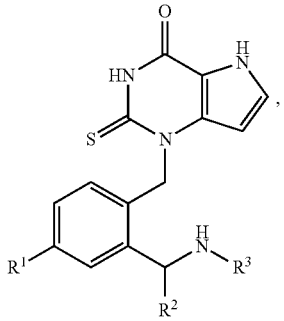

wherein:
R¹ is H, F, Cl or CF₃;
R² is H, CH₃ or C₂H₅; and
R³ is H, CH₃, C₂H₅, n-propyl, isopropyl, n-butyl, isobutyl, sec-butyl, tert-butyl, cyclopropyl, cyclopropylmethyl, cyclobutyl, cyclobutylmethyl or cyclopentyl;
or a pharmaceutically acceptable salt thereof.

13. The method of treatment according to claim 9, wherein the myeloperoxidase inhibitor is:

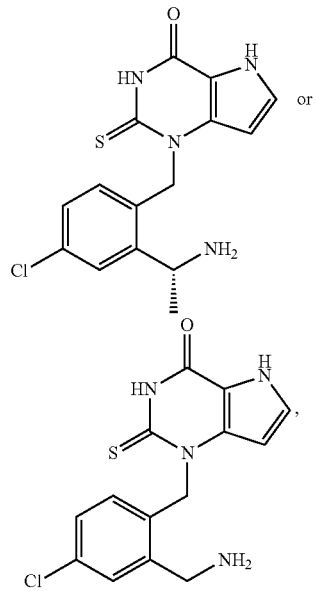

or a pharmaceutically acceptable salt thereof.

* * * * *